(12) United States Patent
Heim et al.

(10) Patent No.: US 8,097,281 B2
(45) Date of Patent: Jan. 17, 2012

(54) COMPOSITION

(75) Inventors: Stefan Heim, Herrenberg (DE); Martina Birgit Schmid, Herrenberg (DE); Christoph Walter Theurer, Herrenberg (DE)

(73) Assignee: GlaxoSmithKline Consumer Healthcare GmbH & Co KG, Buehl (DE)

( * ) Notice: Subject to any disclaimer, the term of this patent is extended or adjusted under 35 U.S.C. 154(b) by 967 days.

(21) Appl. No.: 11/910,937

(22) PCT Filed: Apr. 6, 2006

(86) PCT No.: PCT/EP2006/003530
§ 371 (c)(1),
(2), (4) Date: Oct. 8, 2007

(87) PCT Pub. No.: WO2006/108692
PCT Pub. Date: Oct. 19, 2006

(65) Prior Publication Data
US 2008/0193523 A1  Aug. 14, 2008

(30) Foreign Application Priority Data
Apr. 8, 2005  (GB) ................... 0507167.5

(51) Int. Cl.
*A61K 9/14* (2006.01)
*A61K 9/66* (2006.01)
*A01N 59/03* (2006.01)
*A01N 63/02* (2006.01)

(52) U.S. Cl. ........ 424/489; 424/455; 424/490; 424/496; 424/702; 424/780

(58) Field of Classification Search .................. None
See application file for complete search history.

(56) References Cited

U.S. PATENT DOCUMENTS

| | | | |
|---|---|---|---|
| 3,939,259 A | 2/1976 | Pescetti | 424/20 |
| 4,195,731 A | 4/1980 | Cavazza | 206/222 |
| 4,876,094 A | 10/1989 | Benton et al. | 3/424 |
| 4,902,513 A * | 2/1990 | Carvais | 424/455 |
| 5,272,137 A * | 12/1993 | Blase et al. | 514/54 |
| 5,296,236 A | 3/1994 | Santus et al. | 424/490 |
| 5,595,758 A | 1/1997 | Adusumilli | |
| 5,753,295 A * | 5/1998 | Goldman | 426/590 |
| 5,869,084 A | 2/1999 | Paradissis et al. | 424/439 |
| 6,451,341 B1 * | 9/2002 | Slaga et al. | 424/468 |
| 7,422,758 B2 * | 9/2008 | Block et al. | 424/489 |
| 2002/0114832 A1 * | 8/2002 | Herrmann et al. | 424/461 |
| 2006/0165807 A1 * | 7/2006 | Castan et al. | 424/490 |

FOREIGN PATENT DOCUMENTS

| | | |
|---|---|---|
| EP | 0 468 232 A | 1/1992 |
| EP | 0 820 703 A | 1/1998 |
| EP | 0 854 825 B | 3/2000 |
| EP | 0 963 325 B | 11/2001 |
| WO | WO 98/41217 A1 | 0/1998 |
| WO | WO 01/19901 A | 3/2001 |
| WO | WO 01/72286 A | 10/2001 |
| WO | WO 03/084518 | 10/2003 |

* cited by examiner

*Primary Examiner* — Phyllis G. Spivack
(74) *Attorney, Agent, or Firm* — Dara L. Dinner; Theodore Furman

(57) ABSTRACT

The present invention relates to dosage forms for oral administration of therapeutic formulations, adapted to provide immediate and/or sustained-release of therapeutic substances, particularly for oral administration of vitamins. There is provided a dosage form for oral administration of a vitamin, comprising: a liquid phase containing a vitamin, e.g. Vitamin C in a relatively fast release form and a solid phase suspended in the liquid phase and containing a vitamin e.g. Vitamin C in a relatively slow release form.

25 Claims, No Drawings

COMPOSITION

This application is a §371 application of PCT/EP2006/003530, filed Apr. 6, 2006.

The present invention relates to dosage forms for oral administration of therapeutic formulations, adapted to provide immediate and sustained-release of therapeutic substances, particularly for oral administration of vitamins.

Therapeutic formulations for the oral administration of vitamins e.g. Vitamin C, i.e. ascorbic acid as the free acid or as salts thereof are well known, and are often provided in a solid or liquid formulation for oral administration.

It is frequently desirable to provide therapeutic substances for oral administration in a dosage form which provides sustained release of the therapeutic substance.

By "sustained release" is meant that release of therapeutic substance from the dosage form is controlled such that release of therapeutic substance(s) from the dosage form may maintain an effective plasma concentration of therapeutic substance for a relatively long period of time for example up to 8 hours. By "immediate release" is meant that therapeutic substance is released relatively fast, e.g. such that the therapeutic substance begins to be released immediately the dosage form contacts fluid in the user's gastro-intestinal (GI) tract. Immediate release can achieve a therapeutically active plasma concentration of the therapeutic substance within a relatively short period of time for example 0.5-1 hour. In immediate release, suitably at least 80%, preferably at least 90% and even more preferably at least 95% of the immediate release therapeutic substance is released within 1 hour as determined by the dissolution test for solid dosage forms as described in the European Pharmacopoeia 2005, $3^{th}$ Edition page 228, 2.9.3.

Sustained release dosage forms often comprise a relatively rapid release formulation of the substance, for example an immediate release form, combined with a delayed release formulation, for example from which release of the substance does not occur until the dosage form has reached a predetermined point in the GI tract, or from which release of the substance from the dosage form continues so as to be released slowly over a period of time, e.g. over a period up to 8 hours. By means of a sustained release dosage form, the amount of the therapeutic substance in the user's body can be kept at or above an effective level for a relatively long time.

A common way of delaying release is to coat or encapsulate solid particles containing the substance with a release-delaying coating. For example U.S. Pat. No. 3,939,259, WO-A-01/19901 and WO-A-01/72286 disclose beadlets containing a therapeutic substance and coated with a release-delaying coating, the therapeutic substance in WO-A-01/72286 being a vitamin.

Such delayed release formulations may be made up into a dosage form in various ways. For example U.S. Pat. No. 4,902,513 and WO-A-03/084518 disclose a liquid dosage form which comprises coated delayed release particles containing a therapeutic substance dispersed in a liquid phase which also contains the therapeutic substance in solution, and from which the therapeutic substance is released immediately upon oral administration. U.S. Pat. No. 4,876,094 discloses a sustained-release dosage form comprising coated particles of a therapeutic substance dispersed in a sugar solution with a high viscosity to reduce the rate of settling.

It is an object of this invention to provide an improved therapeutic formulation for oral administration of vitamins, in particular providing the advantage of a sustained release profile.

This invention provides a dosage form for oral administration of a vitamin, comprising:

a liquid phase containing a vitamin in a relatively fast release form and, a solid phase suspended in the liquid phase and containing a vitamin in a relatively slow release form.

The liquid phase may contain a vitamin in an immediate-release form, e.g. in solution or suspension such that the vitamin can begin to be absorbed by the body substantially immediately after oral administration, and the solid phase may contain a vitamin in a delayed release form.

The liquid and solid phases may both contain the same vitamin(s), or the liquid and solid phases may contain different vitamins.

A suitable vitamin, which may be contained in either but preferably both of the liquid and solid phases is Vitamin C (ascorbic acid or a salt thereof). Other suitable vitamins include Vitamin B1, Vitamin B2, Vitamin B6, Vitamin B12, Biotin, Folic Acid, Niacin, Pantothenol; fat soluble vitamins e.g. Vitamin A, Vitamin D, Vitamin E (alpha-tocopherol, typically in the form of alpha-tocopheryl acetate), Vitamin K and Carotenes such as Lutein, Lycopin, beta-carotene, Zeaxanphin. When the vitamin or vitamin mixture comprises riboflavin, it is particularly preferred to use a salt form such as riboflavin phosphate. Suitably the liquid phase may contain Vitamin C and Vitamin E. The Vitamin C may be in the form of ascorbic acid, a salt of ascorbic acid such as sodium ascorbate, or a mixture thereof.

Other therapeutic substances may be included in the dosage form, e.g. the liquid phase or the solid phase or both phases. The liquid and/or solid phase may each contain plural therapeutic substances. Examples of such other therapeutic substances include those known for use in vitamin and multivitamin products, such as coenzymes (e.g. coenzyme Q10), amino acids, fatty acids, isoflavones, minerals, trace elements, sedatives, somniferics, analgesics, antibacterial agents, decongestants and other drugs.

For example the liquid and/or solid phase may contain plural vitamins, e.g. Vitamin C plus Vitamin E, or one or more vitamin plus one or more additional therapeutic substance, such as selenium (preferably as sodium selenate, this oxidation state of selenium being preferred as for example sodium selenite can become insoluble in the presence of the other ingredients of the formulation) and/or zinc (typically as zinc citrate trihydrate).

The liquid phase may contain a therapeutic substance which is particularly suited to immediate release, for example one or more vitamin, trace element, carotinoid such as lycopin, zeaxanthin, lutein, alpha-carotene, beta-carotene, gamma carotene or beta cryptoxanthin; or a mixture thereof.

For example the liquid phase may contain the vitamins Vitamin C, Vitamin E, and preferably selenium and zinc, and the solid phase may contain Vitamin C. Typically the liquid phase may contain 2-10 wt %, typically 4-6 wt %, of vitamin(s), for example 2-4 wt %, e.g. 3.0+/−0.5 wt % of Vitamin C e.g. as ascorbic acid and/or sodium ascorbate or a mixture thereof, and optionally for example also 1-3 wt %, e.g. 2.0+/−0.5 wt % of Vitamin E e.g. as DL-alpha-tocopherol acetate.

Because vitamins are vulnerable to degradation in solution, to achieve a particular quantity of a vitamin in the liquid phase, it is preferred to include an excess overage of the intended quantity of the vitamin in the liquid phase. For example there may be a 50-150, e.g. 100+/−10 wt. % excess of Vitamin C, and/or a 25-100, e.g. 50+/−5 wt % excess of Vitamin E component over the amount aimed at in the liquid phase.

The liquid phase is preferably an aqueous liquid phase and may comprise an amount of 40-90 wt %, typically 40-60 wt %, preferably 45-55 wt % water. Preferably the liquid phase is a viscous aqueous liquid, as a high viscosity is found suitable to enable the solid phase to remain suspended in the liquid phase shortly prior to oral administration so that the solid phase is relatively uniformly distributed throughout the liquid phase. Too low a viscosity can cause the solid phase to precipitate toward the bottom of the liquid phase so as to become concentrated at the bottom of the liquid phase. Too high a viscosity can cause the liquid phase to be too thick to be easily swallowed. The viscosity is suitably such that the solid phase can remain uniformly suspended in the aqueous phase for sufficient time, for example at least 1 minute, for the mixed liquid and solid phases to be orally ingested after mixing the liquid and solid, and optionally agitating the mixture, without the solid phase either settling to the bottom or floating to the top of the liquid phase.

A suitable viscosity range, as measured using a Brookfield Rheometer, Spindle 2 at a temperature of 21° C. at a speed of 20 rpm (i.e. the speed recommended by suppliers of the xanthan gums mentioned herein) is 250-1100 mPa*s, preferably 400-500 mPa*s. At the lower limit of this suitable viscosity range it is found that 50% of the solid phase remains un-sedimented 2 minutes after agitation, and at the lower limit of this preferred viscosity range it is found that 50% of the solid phase remains un-sedimented 6 minutes after agitation.

A suitable viscosity may be achieved by the incorporation of a suitable thickening agent into an aqueous liquid phase. Suitable thickening agents are known in the therapeutic oral formulation field, and typically include: xantham gum (such as those sold under the trade marks Rhodigel™ or Keltrol™ e.g. Rhodigel 80™ or Keltrol F™), gellan gum (E 418), agar (E 406), carrageen (E 407), galactomanan and modified galactomannanas (locust bean gum (E 410), guar gum (E 412), tara gum (E 407), konjac gum, gelatin, arabic gum (E 414), karaya gum (E 416), starch and starch derivatives (such as E 1404, E 1410, E 1412—E 1414, E 1420, E 1422, E 1440, E 1442, E 1450, E 1451), tamarind, traganth (E413), xanthan gum (E415), pectin (E440) and amided pectin (E440ii), cellulose and cellulose derivatives (such as cellulose (E460), microcrystalline cellulose, sodium carboxymethyl cellulose (E466), carboxymethyl cellulose (E466), methyl cellulose (E461), hydroxypropyl cellulose (E463), Methyl ethyl cellulose (E465), hydroxy propyl methyl cellulose (E464), hydroxyethylcellulose), alginates (such as alginic acid (E400), ammonium alginate (E403), calcium alginate (E404), potassium alginate (E402), sodium alginate (E401), propylene glycol alginate (E405), polyvinyl alcohol, ghatii gum, silicates (such as Bentonit (aluminium silicate) or Veegum (magnesium aluminium silicate)), arrowroot, sago, treated Eucheuma alga (E407a), dextran, polyvinyl pyrrolidone (E1201a), polyethylene glycol, acrylic acid polymers (such as polymethacrylic acid, polymethacrylates), and colloidal silicon dioxide (e.g. Aerosil) among others known in the art.

The quantity of thickening agent used to achieve a suitable viscosity may be determined experimentally to enable the solid phase to remain suspended in the liquid phase immediately prior to use as mentioned above. For example in an aqueous phase, when a xantham gum such as Rhodigel 80™ is used as a thickening agent, an amount of the gum in the range 0.25-0.5 wt %, preferably 0.3-0.45 wt % in the aqueous phase is found to be suitable to achieve a uniform suspension of the solid phase, e.g. as described herein, for long enough after shaking the formulation shortly prior to oral administration that the suspension is substantially uniform during oral administration. A suitable viscosity is that corresponding to that provided by such a xantham gum as thickening agent in these ranges.

The density of the liquid phase appears to be less significant than viscosity in achieving suspension of the solid phase in the liquid phase. Suitably an aqueous liquid phase may have a density of 1.0-1.25 g/ml.

In addition to the vitamin(s), water and a suitable thickening agent, the liquid phase suitably also includes one or more of the following ingredients. Sweetener, e.g. sugar e.g. glucose, typically 10-40 wt %. Sugars can themselves thicken an aqueous phase, and the amount of xanthan gum such as Rhodigel 80™ suggested above is suitable to achieve a viscosity in the suitable and preferred ranges mentioned above with this amount of sugar present. Artificial sweeteners such as aspartame, saccharin or cylamate, may be used in a much lower proportion than such viscosity-increasing sugars and may have less effect on the viscosity, such that if such an artificial sweetener instead of such a sugar is used a relatively higher amount of water may be used in the liquid phase. Colourant; such as extract of natural carotene and/or paprika extract, (orange colour) in an amount to achieve a suitable colour, which may be determined empirically. Flavour; such as lemon flavour and/or blood orange extract, in an amount to achieve a suitable flavour, which may be determined empirically. Preservative; such as benzoic acid (E210), sodium benzoate (E211), potassium benzoate (E212), calcium benzoate (E213), sorbic acid (E200), sodium sorbate (E201), potassium sorbate (E202), calcium sorbate (E203), para hydroxybenzoic acid esters (E214, E215, E216, E217, E218, E219), formic acid (E236,E237,E238), propionic acid (E280, E281, E282, E283), biphenyl (E230), ortho phenyl phenol (E231, E232), thiabendazol (E233), grapefruit seed extract, in a conventional amount.

The liquid phase may also contain dietary fibres e.g. prebiotics such as inulin and olegofructose. When present the dietary fibres may be in the range 5 to 70 wt. % such as 10 to 35 wt. %.

The liquid phase described herein constitutes a further aspect of the invention, including particular and preferred features as described above. Accordingly it is an object of the invention to provide a dosage form for oral administration of a vitamin comprising a liquid phase containing a vitamin in a relatively fast release form, but without the solid phase as hereinabove described. The liquid phase provides a carrier for the vitamin and has acceptable organoleptic and mouthfeel properties. In one embodiment the unpleasant astringent properties of certain components such as zinc and/or selenium have been significantly masked.

When present, the solid phase in a dosage form according to the invention, may comprise the vitamin in combination with an acid, suitably a solid water soluble acid, e.g. a carboxylic acid such as tartaric acid, as such acids are known to stabilise vitamins such as vitamin C. Typically the proportion of such an acid in the solid phase may be 0.1-1.0 wt %, for example 0.2-0.3 wt % of the weight of the vitamin in the solid phase.

The solid phase suitably is in the form of pellets, typically spherical, suitably 0.5-1.5 mm, e.g. ca. 1.0+/−0.1 mm diameter, or other shapes of equivalent volume. Typically such pellets may comprise 75-99 wt %, e.g. 80-85 wt % of the vitamin(s), for example Vitamin C, e.g. in the form of ascorbic acid.

Suitably such pellets may comprise one or more vitamin-containing layer deposited on a core particle, and may be made by known pelleting processes, for example as disclosed in U.S. Pat. No. 3,939,239 by building up a layer containing the vitamin surrounding a pellet core particle typically made of an inert material such as maize starch and/or sucrose. For example Spansule® technology developed in the 1950's, and still used today utilizes sugar-based core particles in which vitamin may be incorporated directly or may be dusted or otherwise distributed over the particle surface, e.g. building up layers comprising the vitamin. Typically such a core may comprise a substantially spherical particle typically 35-40 mesh (425-500 microns) size comprising a compacted mixture of sugar and maize starch. Methods of making such cores are well known, and suitable specifications for them are for example disclosed in standard pharmaceutical literature e.g. the US Pharmacopoeia and the National Formulary. Such cores are commercially available e.g. from NP Pharm (Bazainville, FR).

The vitamin and other components (if present) of the solid phase such as the above-mentioned acid may be deposited upon such a core by a generally known powder layering process. Typically in such a process the cores may be initially sprayed with a mixture of shellac and the acid in a suitable solvent, typically ethanol. This applied mixture is then allowed to dry e.g. in an air stream, leaving a tacky coating on the core. These coated cores may then be dusted with the powdered vitamin such as ascorbic acid to thereby deposit a layer of the vitamin powder. The vitamin-coated cores may then be sprayed with another coating of the mixture of shellac, tartaric acid and solvent, and this coating is then allowed to dry as before, then another layer of the powdered vitamin is dusted onto the cores e.g. in a rotating pan. This process is repeated until the desired amount of the vitamin has been deposited onto the cores. Vitamin-containing pellets made in this way are known and commercially available.

The pellet is preferably provided with a release-delaying coating to delay release of the vitamin into the digestive tract. Dispersion of the vitamin from such coated pellets may for example be delayed by the need for water and/or the vitamin to diffuse through the coating, or by the need for the coating to be dissolved, rendered permeable, breached or at least partly removed by contact with fluid in the GI tract. Release of vitamin from such coated pellets may be controlled by controlling the thickness and/or composition of the coating material.

Methods of applying a release-delaying coating to such pellets are well known, for example by spraying or pouring a solution of the coating material onto the pellets. Other methods of applying the release-delaying coating are known, for example as disclosed in U.S. Pat. No. 3,939,259 e.g. by placing uncoated pellets containing the vitamin in a revolving pan and contacting the pellets with sufficient coating solution to cover the pellets, followed by drying the coated pellets.

Numerous suitable release-delaying coatings are known in the art. Typically the coating may be a coating that allows diffusion of substances through or an erodable coating. The release-delaying characteristics of the coating may be independent of the pH of the GI environment of the coating, or dependent on GI pH such as the so-called enteric coating that is substantially resistant under gastric conditions but is eroded during passage through the small intestine.

Examples of release-delaying coating materials include; cellulose acetate, cellulose acetate phthalate, cellulose acetate trimellitate, hydroxy propyl methyl cellulose acetate succinate, hydroxy propyl methyl cellulose phthalate, polyvinyl acetate phthalate, carboxy methyl ethyl cellulose, shellac, ethyl cellulose, polyvinyl acetate, Eudragits™, such as Eudragit L 12,5 (solution), Eudragit L 100 (powder), Eudragit S 12,5 (solution), Eudragit S 100 (powder): anionic polymers based on methacrylic acid and methacrylates with —COOH functional groups, Eudragit L 100-55 (powder) and Eudragit L30 D-55 (solution): anionic polymers of methacrylic acid and ethacrylates with —COOH functional groups, Eudragit RL (RL 12.5, RL100, RL PO, RL 30 D) and Eudragit RS (RS 12.5, RS 100, RS PO, RL 30 D): Copolymers of acrylate and methacrylates with quarternary ammonium groups as functional group.

Shellac, optionally containing talc to assist slow permeation of water through the shellac, is a preferred pH independent release delaying coating. Typically such a release delaying coating may comprise shellac containing 30-50 wt % of talc, typically 40+/−5 wt %

The coating operation is continued until the pellets have a suitable delayed release profile, for example as determined using the above-mentioned European Pharmacopoeia dissolution test, for example so that after 1 hour 15-30%, after 4 hours 45-70%, and after 8 hours more than 70% of the vitamin content is released into solution. The achievement of a suitable coating may be determined by sampling during the coating operation and applying such a dissolution test. Alternative methods of making particles of the above-mentioned size with such a delayed release profile will be apparent to those skilled in the art.

For pellets of the dimensions mentioned above a suitable coating may be provided by a coated pellet in which the coating material, e.g. shellac comprises ca. 5-10 wt % of the coated pellet.

The solid phase may further comprise live microorganisms as for example probiotic bacteria e.g. lactobacillus strains such as *L. Acidophilus, L. Bulgaricus, L. Bifidus, L. Rhamnosus, L. Plantarum, L. Salivarius, L. Lactis, L. Casei, L. Brevis, L. reuteri, L. sporogenes*; or bifidobacteria strains such as *B. Bifidum, B. Infantis, B. Longum, B. Breve*. Suitably the content of live micro-organisms is between $10^7$ and $10^{10}$ organisms per unit dose e.g. between $10^8$ and $10^9$ per unit dose. The microorganisms may be combined with other optional ingredients for example to improve the acid tolerance of the microorganisms. A suitable additional ingredient could be a polysaccharide or another matrix material e.g. HPMC. The microorganisms and optional other ingredients may be provided as a pure powder mixture or as granules or pellets, for combination with other components of the solid phase, such as a vitamin.

One aspect of the present invention is that it provides a dosage form including a solid phase that may be admixed with a liquid phase, just prior to consumption. This can be advantageous when seeking to provide a drinkable product having a long shelf life, as may be desired with a product suitable for commercialization. For example probiotic bacteria are sensitive to moisture and so the shelf-life of a liquid or semi-liquid product containing such bacteria, is normally fairly short. In contrast, according to the present invention, bacteria may be stored in a dry form, in the solid phase, and so a much longer shelf-life may be achieved than would otherwise be possible In the dosage form of this invention the wt.:wt. ratio of liquid phase: solid phase may typically be in the range 10-30: 1, for example 20+/−5:1.

The dosage form of this invention may contain a unit dose of one or more vitamin for example 0.5-2.5 g, for example 0.75-2.0 g of one or more vitamin, e.g. of Vitamin C, or of Vitamins C and E. Typically the vitamin may be divided between the liquid: solid phases in a weight:weight ratio in the range 1:1-1:3, for example 1:1-1:2, preferably 1:1.5+/− 0.5. Typically the volume of the liquid phase for use as such a unit dose may be 10-30 ml, for example 15+/−2 ml.

The dosage form of this invention may be provided in a variety of forms of packages, for example a container (e.g. a sachet) containing the solid phase, and a separate container (e.g. bottle or vial) containing the liquid phase, and from which suitable quantities of the solid and liquid phases may be dispensed and mixed, with suitable agitation to suspend the solid phase in the liquid phase prior to oral administration.

A preferred package comprises a first compartment containing the liquid phase and a second compartment containing the solid phase, the first and second compartments being non-communicating prior to administration of the formulation, so as to keep the liquid and solid phases separate, and able to be brought into communication to enable the liquid and solid phases to be mixed for administration of the dosage form.

When provided in such a package the dosage form of the invention offers the advantage that combinations of different vitamins and/or therapeutic substances, including those which are usually incompatible with each other, may be incorporated in the package kept out of communication in the respective first and second compartments before the compartments are brought into communication, which may be very shortly before oral administration.

In an embodiment such a package may comprise a container, such as a bottle or vial defining a first compartment suitable to contain the liquid phase and having an upper mouth opening, a capsule defining a second compartment suitable to contain the solid phase mounted in the mouth opening and having a frangible wall between the interior of the container and the interior of the capsule, the package being provided with a breach means to breach the frangible wall to thereby bring the compartments into communication to cause the liquid and solid phases to be mixed for administration of the dosage form. Suitably the breach means may comprise a cutting element adapted to be operated by a user of the package to cut the frangible wall. Suitably the package comprises a closure which may be opened when the compartments have been brought into communication and the liquid and solid phases have been mixed for administration of the dosage form. Suitably the closure is operably connected to the breach means.

A suitable package of this embodiment is for example disclosed in EP-B-0 963 325, in which the container is represented (1) having upper mouth (2), capsule (3), frangible wall (4), cutting element (11) and closure (13) operably connected to cutting element (11) as described therein. When such a package is used the solid phase, e.g. the above described delayed release pellets, may be separately respectively contained in the capsule (3) and the liquid phase in the container (1) out of communication as shown in FIG. 2 of EP-B-0 963 325. Shortly prior to use the closure (13) may be operated as shown in FIGS. 3 and 4 of EP-B-0 963 325 to bring the capsule (3) and container (1) into communication so that the solid phase falls into the liquid phase. The combined liquid phase and solid phase may then be agitated to disperse the solid phase in the liquid phase, uniform suspension of the solid phase in the liquid phase being facilitated by the above-mentioned preferred viscosity of the liquid phase. The combined liquid phase and solid phase may then be ingested orally by the user. A similar package is for example disclosed in U.S. Pat. No. 4,195,731. Such packages may be made of known plastics materials known to be compatible with the liquid and solid phase.

In another embodiment such a package may comprise a container, such as a bottle or vial defining a first compartment suitable to contain the liquid phase and having an upper mouth opening, a capsule defining a second compartment suitable to contain the solid phase mounted in the mouth opening and having a valve means between the interior of the container and the interior of the capsule, the package being provided with a valve opening means to open the valve to thereby bring the compartments into communication to cause the liquid and solid phases to be mixed for administration of the dosage form. Suitably the package comprises a closure which may be opened when the compartments have been brought into communication and the liquid and solid phases have been mixed for administration of the dosage form. Suitably the closure is operably connected to the valve opening means.

A suitable package of this embodiment is for example disclosed in EP-B-0 854 825, in which the container is represented (1) having upper mouth, a capsule (2), valve means (3), and closure (4) operably connected to valve means (3) as described therein. When such a package is used the solid phase, e.g. the above described delayed release pellets, may be separately respectively contained in the capsule (2) and the liquid phase in the container (1) out of communication as shown in FIG. 1 of EP-B-0 854 825. Shortly prior to use the closure (4) may be operated as shown in FIGS. 2 and 3 of EP-B-0 854 825 to open valve means (3) to thereby bring the capsule (2) and container (1) into communication so that the solid phase falls into the liquid phase. The combined liquid phase and solid phase may then be agitated to disperse the solid phase in the liquid phase, uniform suspension of the solid phase in the liquid phase being facilitated by the above-mentioned preferred viscosity of the liquid phase. The combined liquid phase and solid phase may then be ingested orally by the user.

The invention will now be described by way of example only.

EXAMPLE 1

Liquid Phase

A liquid phase was prepared having the following nominal composition per unit dose:

| Ingredient | Function | Quantity g |
| --- | --- | --- |
| Water (drinking water standard) | Vehicle | 7.3761 |
| Glucose monohydrate (Ph. Eur) | Sweetener | 5.500 |
| Extract of natural carotene | Colour | 0.0150 |
| Paprika extract | Colour | 0.0150 |
| Potassium sorbate (Ph. Eur) | Preservative | 0.0150 |
| Sodium benzoate | Preservative | 0.0090 |
| Xanthan gum (Rhodigel 80) | Thickener | 0.0525 |
| Lemon flavour | Flavour | 0.0600 |
| Blood orange extract | Flavour | 0.1455 |
| Sodium ascorbate E 301 (Vitamin C) (USP) | Vitamin | 0.2812 |
| Ascorbic acid (Vitamin C) (Ph.Eur) | Vitamin | 0.1500 |
| Sodium selenate | therapeutic substance | 0.0002 |
| Zinc citrate trihydrate | therapeutic substance | 0.0641 |
| DL-alpha Tocopheryl acetate (Vitamin E) 50% concentrate (Ph. Eur). Consisting of: Silica, colloidal anhydrous (Ph.Eur) 0.0060 g; Maltodextrin (Ph.Eur) 0.1461 g; Food starch, modified (FCC) 0.1461 g; DL-alpha Tocopheryl acetate (Ph.Eur) 0.2981 g | Vitamin | 0.5961 |
| Total weight of liquid phase | | 14.2797 g |

Because vitamins are vulnerable to degradation in solution a 100 wt. % excess of the Vitamin C components and a 50 wt % excess of the Vitamin E component over the amount stated in the table above was included in the liquid phase, bringing the total weight per unit dose up to 15 g.

The liquid phase was prepared as follows. Water was heated to 70° C. then all the non temperature-sensitive ingredients were added, e.g. glucose and preservative. The mixture was stirred at this temperature for a few minutes until mixing was complete, and then allowed to cool to ambient temperature. The ascorbic acid and sodium ascorbate was then added (weights as in table plus the above-mentioned excesses per 15 g of liquid phase) and the mixture stirred until these had dissolved, then the mixture was passed through a micro filter. Then, whilst stirring, the zinc citrate, paprika extract, extract of natural carotene, blood orange extract, lemon flavour, DL-alpha Tocopheryl acetate and xanthan gum was added. This mixture was then contained as 15.00 g aliquots in containers as disclosed in EP-B-0 963 325.

Solid Phase

A solid phase was prepared having the following composition per 0.7255 g unit dose:

| Ingredient | Function | Quantity g |
|---|---|---|
| Ascorbic acid (Vitamin C) (Ph.Eur) | Vitamin | 0.600 |
| Tartaric acid (Ph.Eur) | Stabilizer | 0.0016 |
| Maize starch (Ph. Eur) | Pellet core component | 0.0122 |
| Sucrose (Ph. Eur) | Pellet core component | 0.0487 |
| Talc | Coating component | 0.0120 |
| Shellac, dewaxed (Ph. Eur) | Coating component | 0.051 |
| Total wt. of solid phase unit dose | | 0.7255 g |

The solid phase was prepared by preparing pellet cores of the maize starch and sucrose, then building up layers of ascorbic acid to form pellets. A delayed release layer of shellac was then applied.

A generally known procedure was used to make these pellets. Starting with 35-40 mesh (425-500 micron) commercially available (NP Pharm) pellet cores comprising the maize starch and the sucrose, these were initially sprayed with an ethanolic mixture of shellac and tartaric acid, then this applied mixture was allowed to dry, leaving a tacky shellac outer coating. The coated cores were then dusted with the powdered ascorbic acid to deposit a layer of the powder. These vitamin-coated cores were then sprayed with another coating of the ethanolic mixture of shellac and tartaric acid, this coating was then allowed to dry as before, then another layer of the powdered ascorbic acid was dusted onto the cores e.g. in a rotating pan. This process was repeated until the desired amount of the vitamin has been deposited onto the cores. Finally an outermost coating layer of shellac containing ca. 42 wt % of talc was applied as a release-delaying coating by a pan coating technique using an ethanol solution of shellac, and powdering the talc onto the pellets.

The coated pellets produced by this operation had a diameter ca. 1 mm and had a delayed release profile as determined using the above-mentioned European Pharmacopoeia 2005 dissolution test, such that after 1 hour 15-30%, after 4 hours 45-70%, and after 8 hours more than 70% of the vitamin content was released into solution. The achievement of a suitable coating was determined by sampling of pellets during the coating operation and subjecting them to this dissolution test.

These pellets were then contained as 0.7255 g aliquots in packages of the containers as disclosed in EP-B-0 963 325.

It was found that when the solid phase was added to the liquid phase the viscosity of the liquid phase was such that the pellets remained suspended uniformly in the liquid phase until the mixture was orally ingested.

EXAMPLE 2

Tables 1 and 2 below show the influence of the viscosity of the liquid phase, as measured using a Brookfield Rheometer, Spindle 2 at a temperature of 21° C. at various speeds, on the suspension of the pellets in the liquid phase. In Table 1 the liquid phase has the composition as listed above, i.e. including glucose. In Table 2 the glucose was omitted, the amount of other ingredients being as listed above.

From Tables 1 and 2 it can be seen that with Xanthan concentrations in the range 0.3-0.45 wt % the pellets of the solid phase remain suspended in the liquid phase for 6 minutes or more after mixing and agitation.

TABLE 1

| | | Glucose present in liquid phase | | | | | |
|---|---|---|---|---|---|---|---|
| Xanthan Concn. | Density | Viscosity mPa * s | | | | Flotation of pellets | |
| wt % | g/ml | 10 rpm | 20 rpm | 50 rpm | 100 rpm | 50% sedimented | 90% sedimented |
| 0.15 | 1.195 | — | 216 | 140 | 112 | <1 minute | >15 minutes |
| 0.20 | 1.196 | — | 220 | 147 | 117 | <1 minute | >15 minutes |
| 0.25 | 1.196 | 408 | 284 | 181 | 143 | <1 minute | >15 minutes |
| 0.30 | 1.196 | 692 | 462 | 270 | 192 | 6 minutes | >15 minutes |
| 0.35 | 1.196 | 1380 | 850 | 466 | 302 | >15 min <20 hours | <20 hours |
| 0.40 | 1.197 | 1450 | 905 | 498 | 324 | >15 min <20 hours | <20 hours |
| 0.45 | 1.198 | 1790 | 1100 | 590 | 378 | >15 min <20 hours | <20 hours |

TABLE 2

No glucose in liquid phase

| Xanthan Concn. Wt % | Density g/ml | Viscosity mPa * s | | | | Flotation of pellets | |
|---|---|---|---|---|---|---|---|
| | | 10 rpm | 20 rpm | 50 rpm | 100 rpm | 50% sedimented | 90% sedimented |
| 0.15 | 1.043 | — | — | — | 43 | <1 minute | 2 minutes |
| 0.20 | 1.040 | — | — | — | 45.4 | <1 minute | 2 minutes |
| 0.25 | 1.041 | — | 224 | 125 | 87.8 | <1 minute | 2.5 minutes |
| 0.30 | 1.041 | 434 | 278 | 150 | 103 | 2 minutes | <60 minutes |
| 0.35 | 1.041 | 960 | 560 | 284 | 172 | 2 hours | >5 hours |
| 0.40 | 1.041 | 1130 | 660 | 336 | 201 | 4 hours | >5 hours |
| 0.45 | 1.047 | 1180 | 700 | 354 | 215 | 4 hours | >5 hours |

EXAMPLE 3

Liquid Phase

A liquid phase is prepared having the following nominal composition per unit dose:

| Ingredient | Function | Quantity g |
|---|---|---|
| Water (drinking water standard) | Vehicle | 9.1711 |
| Oligo fructose | Prebiotic | 5.0000 |
| Extract of natural carotene | Colour | 0.0150 |
| Paprika extract | Colour | 0.0150 |
| Potassium sorbate (Ph. Eur) | Preservative | 0.0250 |
| Xanthan gum | Thickener | 0.0263 |
| Lemon flavour | Flavour | 0.0600 |
| Blood orange extract | Flavour | 0.1455 |
| Sodium ascorbate E 301 (Vitamin C) (USP) | Vitamin | 0.2700 |
| Ascorbic acid (Vitamin C) (Ph.Eur) | Vitamin | 0.2400 |
| Zinc citrate trihydrate | therapeutic substance | 0.0321 |
| Total weight of liquid phase | | 15.000 g |

The liquid phase may be prepared as follows:

Heat the water to 70° C. and add the non-temperature sensitive ingredients; maintain at that temperature for 2 hours. Cool the liquid down to 50° C. and add the more temperature sensitive ingredients, namely the prebiotic fibres (oligo fructose) and the preserving agent (potassium sorbate) and stir for 120 min. Cool down the liquid to room temperature and add ascorbic acid and sodium ascorbate. Filter the solution to reduce the risk of a microbiological contamination (sterile filtration or germ reducing filtration). Add zinc citrate trihydrate, flavours and xanthan gum for 2 hours. Fill the resulting liquid into bottles.

Solid Phase

A solid phase is prepared having the following nominal composition per unit dose:

| Ingredient | Function | Quantity g |
|---|---|---|
| Ascorbic acid (Vitamin C) (Ph.Eur) | Vitamin | 0.06000 |
| Tartaric acid (Ph.Eur) | stabiliser | 0.00016 |
| Maize starch (Ph. Eur) | Pellet core component | 0.00122 |
| Sucrose (Ph. Eur) | Pellet core component | 0.00487 |
| Talc | Coating component | 0.00120 |
| Shellac, dewaxed (Ph. Eur) | Coating component | 0.00510 |
| Probiotic bacteria powder (5 × $10^9$ live probiotic per 0.5 g) | Probiotic bacteria | 0.50000 |
| Total wt. of solid phase unit dose | | 0.57255 g |

The solid phase containing Vitamin C pellets may be prepared as per the methodology of Example 1, and filled into containers as disclosed in EP-B-0 963 325. The probiotic bacteria powder, identified above as one of the ingredients of the solid phase, is obtainable from a supplier such as Christian Hansen, Denmark, and is separately loaded into the containers.

The invention claimed is:

1. A dosage form for oral administration of a vitamin comprising an aqueous liquid phase comprising 40-90 wt % water containing at least one vitamin in an immediate-release form and, a solid phase suspended in the liquid phase and containing at least one vitamin in a delayed release form and wherein the liquid phase has a viscosity, as measured using a Brookfield Rheometer, Spindle 2 at a temperature of 21° C. at a speed of 20 rpm, in the range 250-1100 mPa*s.

2. The dosage form according to claim 1 wherein the liquid and solid phases both contain a vitamin which is Vitamin C, and, optionally, both phases contain Vitamin E and/or selenium as sodium selenate.

3. The dosage form according to claim 2 wherein the liquid phase contains Vitamin C, and Vitamin E, and further comprises selenium and zinc.

4. The dosage form according to claim 3 wherein the liquid phase contains 2-4 wt % of Vitamin C and 1-3 wt % of Vitamin E.

5. The dosage form according to claim 4 wherein the liquid phase contains a 50-150 wt % excess of Vitamin C, and/or 25-100 wt % excess of Vitamin E over said 2-4 wt % of Vitamin C and also 1-3 wt % of Vitamin E.

6. The dosage form according to claim 1 wherein the liquid phase contains 2-10 wt % of the vitamin.

7. The dosage form according to claim 1 wherein the liquid phase has a viscosity, as measured using a Brookfield Rheometer, Spindle 2 at a temperature of 21° C. at a speed of 20 rpm, in the range of 400-500 mPa*s.

8. The dosage form according to claim 1 which further includes a thickening agent which is xanthan gum.

9. The dosage form according to claim 8 wherein the xanthan gum is present in the range of 0.25-0.5 wt % in the aqueous phase.

10. The dosage form according to claim 1 wherein the solid phase comprises the vitamin in combination with an acid which is a solid water soluble carboxylic acid.

11. The dosage form according to claim 10 wherein the proportion of the acid in the solid phase is 0.1-1.0 wt % of the weight of the vitamin in the solid phase.

12. The dosage form according to claim 1 wherein the solid phase is in the form of pellets which are spherical of 0.5-1.5 mm diameter, or another shape of equivalent volume.

13. The dosage form according to claim 12 wherein said pellets comprise 75-99 wt % of the vitamin(s).

14. The dosage form according to claim 12 wherein said pellets are provided with a release-delaying coating to delay release of the vitamin into the digestive tract.

15. The dosage form according to claim 14 wherein said release-delaying coating comprises shellac containing talc.

16. The dosage form according to claim 1 wherein the w/w ratio of liquid phase:solid phase is in the range 10-30:1.

17. The dosage form according to claim 1 wherein the vitamin is divided between the liquid:solid phases in a weight:weight ratio in the range 1:1-1:3.

18. The dosage form according to claim 1 provided in a package which comprises a first compartment containing the liquid phase and a second compartment containing the solid phase, the first and second compartments being non-communicating prior to administration of the dosage form, and able to be brought into communication to enable the liquid and solid phases to be mixed for administration of the dosage form.

19. The dosage form according to claim 1 further comprising a prebiotic in the liquid phase.

20. The dosage form according to claim 1 further comprising a probiotic in the solid phase.

21. A dosage form for oral administration of a vitamin, in the form of an aqueous liquid phase comprising 40 to 90 wt % water and the vitamin, and optionally zinc and selenium as sodium selenate in an immediate release form, the liquid phase having a viscosity, as measured using a Brookfield Rheometer, Spindle 2 at a temperature of 21° C. at a speed of 20 rpm, in the range 250-1100 mPa*s.

22. The dosage form according to claim 21 wherein the liquid phase contains 2 to 10 wt % of vitamin.

23. The dosage form according to claim 21 wherein the viscosity is in the range 400-500 mPa*s.

24. The dosage form according to claim 21 which further includes a thickening agent which is xanthan gum.

25. The dosage form according to claim 24 wherein the xanthan gum is present in the range of 0.25-0.5 wt % in the liquid phase.

\* \* \* \* \*